(12) United States Patent
Krishnan

(10) Patent No.: US 7,491,753 B2
(45) Date of Patent: Feb. 17, 2009

(54) ANTIMICROBIAL AND ANTISTATIC POLYMERS AND METHODS OF USING SUCH POLYMERS ON VARIOUS SUBSTRATES

(75) Inventor: Venkataram Krishnan, Cary, NC (US)

(73) Assignee: Mallard Creek Polymers, Inc., Chalotte, NC (US)

( * ) Notice: Subject to any disclaimer, the term of this patent is extended or adjusted under 35 U.S.C. 154(b) by 581 days.

(21) Appl. No.: 10/882,570

(22) Filed: Jul. 1, 2004

(65) Prior Publication Data

US 2005/0003163 A1      Jan. 6, 2005

Related U.S. Application Data

(60) Provisional application No. 60/484,745, filed on Jul. 3, 2003.

(51) Int. Cl.
*C09D 5/16*     (2006.01)
(52) U.S. Cl. ................ 523/122; 524/543; 524/555
(58) Field of Classification Search ............... 523/122; 524/543, 555
See application file for complete search history.

(56) References Cited

U.S. PATENT DOCUMENTS

| | | |
|---|---|---|
| 2,882,157 A | 4/1959 | Thompson et al. |
| 2,972,535 A | 2/1961 | Laasko et al. |
| 3,140,227 A | 7/1964 | Roth et al. |
| 3,227,672 A | 1/1966 | Fertig et al. |
| 3,262,807 A | 7/1966 | Sterman et al. |
| 3,296,167 A | 1/1967 | Turner et al. |
| 3,296,196 A | 1/1967 | Lamoreaux |
| 3,450,794 A | 6/1969 | Ebneth et al. |
| 3,592,805 A | 7/1971 | Szabo et al. |
| 3,619,200 A | 11/1971 | Ferguson et al. |
| 3,753,716 A | 8/1973 | Ishihara et al. |
| 3,872,128 A | 3/1975 | Byck |
| 4,017,440 A | 4/1977 | Killam |
| 4,026,941 A | 5/1977 | Login et al. |
| 4,029,694 A | 6/1977 | Weipert et al. |
| 4,070,189 A | 1/1978 | Kelley et al. |
| 4,080,315 A | 3/1978 | Login |
| 4,081,419 A | 3/1978 | Shimizu |
| 4,093,676 A | 6/1978 | Weipert et al. |
| 4,098,842 A | 7/1978 | Login |
| 4,104,443 A | 8/1978 | Latta et al. |
| 4,147,550 A | 4/1979 | Campbell et al. |
| 4,226,748 A | 10/1980 | Matsunaga et al. |
| 4,229,554 A | 10/1980 | Newkirk et al. |
| 4,234,381 A | 11/1980 | Killam |
| 4,256,800 A | 3/1981 | Stockhausen et al. |
| 4,332,919 A | 6/1982 | Kobayashi et al. |
| 4,361,623 A | 11/1982 | Newkirk et al. |
| 4,366,238 A | 12/1982 | Yokoyama et al. |
| 4,377,667 A | 3/1983 | Sakurai et al. |
| 4,384,078 A | 5/1983 | Ohya et al. |
| 4,416,668 A | 11/1983 | Thompson |
| 4,500,517 A | 2/1985 | Luss |
| 4,506,070 A | 3/1985 | Ben |
| 4,543,390 A | 9/1985 | Tanaka et al. |
| 4,546,140 A | 10/1985 | Shih |
| 4,617,343 A | 10/1986 | Walker et al. |
| 4,632,881 A | 12/1986 | Trotz et al. |
| 4,668,748 A | 5/1987 | Hardam et al. |
| 4,722,965 A | 2/1988 | Wong et al. |
| 4,735,991 A | 4/1988 | Guioth et al. |
| 4,740,546 A | 4/1988 | Masuda et al. |
| 4,810,567 A | 3/1989 | Calcaterra et al. |
| 4,831,098 A | 5/1989 | Watanabe et al. |
| 4,841,021 A | 6/1989 | Katritzky et al. |
| 4,857,585 A | 8/1989 | Leising |
| 4,857,590 A | 8/1989 | Gaggar et al. |
| 4,859,727 A | 8/1989 | Sasaki et al. |
| 4,877,687 A | 10/1989 | Azegami et al. |
| 4,891,306 A | 1/1990 | Yokoyama et al. |
| 4,898,908 A | 2/1990 | Lahalih et al. |
| 4,900,543 A | 2/1990 | Ritter et al. |
| 4,900,544 A | 2/1990 | Ritter et al. |
| 4,920,166 A | 4/1990 | Buysch et al. |

(Continued)

FOREIGN PATENT DOCUMENTS

DE      2447611      4/1975

(Continued)

OTHER PUBLICATIONS

Appendini et al. "Review of antimicrobial food packaging", *Innovative Food Science & Emerging Technologies* 3:113-126 (2002).

(Continued)

*Primary Examiner*—Edward J Cain
(74) *Attorney, Agent, or Firm*—Womble Carlyle Sandridge & Rice PLLC

(57) ABSTRACT

The present invention relates to a substrate having antimicrobial and/or antistatic properties. Such properties are imparted by applying a coating or film formed from a cationically-charged polymer composition. The polymer composition includes a noncationic ethylenically unsaturated monomer, an ethylenically unsaturated monomer capable of providing a cationic charge to the polymer composition, and a steric stabilization component incorporated into the cationically-charged polymer composition. The present invention also relates to a polymeric material comprising a base polymer blended with the above cationically-charged polymer composition.

47 Claims, No Drawings

U.S. PATENT DOCUMENTS

| | | |
|---|---|---|
| 4,931,506 A | 6/1990 | Yu |
| 4,943,612 A | 7/1990 | Morita et al. |
| 4,948,720 A | 8/1990 | Chen et al. |
| 4,954,636 A | 9/1990 | Merianos et al. |
| 4,981,936 A | 1/1991 | Good et al. |
| 4,997,697 A | 3/1991 | Malhotra |
| 4,999,249 A | 3/1991 | Deschler et al. |
| 5,010,139 A | 4/1991 | Yu |
| 5,024,840 A | 6/1991 | Blakely et al. |
| 5,043,195 A | 8/1991 | Skrivseth |
| 5,059,629 A | 10/1991 | Patton et al. |
| 5,061,752 A | 10/1991 | Buysch et al. |
| 5,081,182 A | 1/1992 | Robinson et al. |
| 5,142,010 A | 8/1992 | Olstein |
| 5,153,321 A | 10/1992 | Finter et al. |
| 5,175,059 A | 12/1992 | Yamamoto et al. |
| 5,194,539 A | 3/1993 | Charmot et al. |
| 5,247,008 A | 9/1993 | Michels et al. |
| 5,290,894 A | 3/1994 | Melrose et al. |
| 5,312,863 A | 5/1994 | Van Rheenen et al. |
| 5,314,924 A | 5/1994 | Lee |
| 5,346,956 A | 9/1994 | Gnanou |
| 5,358,688 A | 10/1994 | Robertson |
| 5,369,179 A | 11/1994 | Havens |
| 5,370,981 A | 12/1994 | Krafft et al. |
| 5,403,640 A | 4/1995 | Krishnan et al. |
| 5,403,883 A | 4/1995 | Messner et al. |
| 5,447,643 A | 9/1995 | Kelkenberg et al. |
| 5,494,987 A | 2/1996 | Imazato et al. |
| 5,515,117 A | 5/1996 | Dziabo et al. |
| 5,518,788 A | 5/1996 | Invie |
| 5,520,910 A | 5/1996 | Hashimoto et al. |
| 5,536,494 A | 7/1996 | Park |
| 5,536,861 A | 7/1996 | Robertson |
| 5,591,799 A | 1/1997 | Bott et al. |
| 5,608,021 A | 3/1997 | Uchiyama et al. |
| 5,645,968 A | 7/1997 | Sacripante |
| 5,654,369 A | 8/1997 | Tsubaki et al. |
| 5,700,742 A | 12/1997 | Payne |
| 5,773,507 A | 6/1998 | Incorvia et al. |
| 5,798,048 A | 8/1998 | Ries |
| 5,830,934 A | 11/1998 | Krishnan |
| 5,830,983 A | 11/1998 | Alex et al. |
| 5,834,561 A | 11/1998 | Fukumoto et al. |
| 5,849,822 A | 12/1998 | Kido et al. |
| 5,886,098 A | 3/1999 | Ueda et al. |
| 5,967,714 A | 10/1999 | Ottersbach et al. |
| 5,997,815 A | 12/1999 | Anders et al. |
| 6,022,553 A | 2/2000 | Anders et al. |
| 6,039,940 A | 3/2000 | Perrault et al. |
| 6,045,919 A | 4/2000 | Alex et al. |
| 6,050,979 A | 4/2000 | Haemmerle et al. |
| 6,090,459 A | 7/2000 | Jadamus et al. |
| 6,096,800 A | 8/2000 | Ottersbach et al. |
| 6,103,368 A | 8/2000 | Fukuda et al. |
| 6,127,105 A | 10/2000 | Vandenabeele |
| 6,187,856 B1 | 2/2001 | Incorvia et al. |
| 6,194,530 B1 | 2/2001 | Klesse et al. |
| 6,197,322 B1 | 3/2001 | Dutkiewicz et al. |
| 6,203,856 B1 | 3/2001 | Ottersbach et al. |
| 6,207,361 B1 | 3/2001 | Greener et al. |
| 6,218,492 B1 | 4/2001 | Hill et al. |
| 6,242,526 B1 | 6/2001 | Siddiqui et al. |
| 6,248,811 B1 | 6/2001 | Ottersbach et al. |
| 6,251,967 B1 | 6/2001 | Perichaud et al. |
| 6,266,490 B1 | 7/2001 | Mukai et al. |
| 6,280,509 B1 | 8/2001 | Mallow |
| 6,319,883 B1 | 11/2001 | Graham et al. |
| 6,368,587 B1 | 4/2002 | Anders et al. |
| 6,410,040 B1 | 6/2002 | Melrose et al. |
| 6,428,866 B1 | 8/2002 | Jadamus et al. |
| 6,482,781 B2 | 11/2002 | Graham et al. |
| 6,497,868 B1 | 12/2002 | Tanahashi |
| 6,500,981 B1 | 12/2002 | Weipert |
| 6,525,134 B1 | 2/2003 | Lacroix et al. |
| 6,767,647 B2 | 7/2004 | Swofford et al. |
| 6,797,743 B2 | 9/2004 | McDonald |
| 2001/0007694 A1 | 7/2001 | Ottersbach et al. |
| 2001/0050478 A1 | 12/2001 | Schmitz |
| 2002/0037955 A1 | 3/2002 | Baumann et al. |
| 2002/0081923 A1 | 6/2002 | Artley et al. |
| 2002/0139583 A1 | 10/2002 | Masui et al. |
| 2002/0168473 A1 | 11/2002 | Ottersbach et al. |
| 2002/0177828 A1 | 11/2002 | Batich et al. |
| 2003/0013624 A1 | 1/2003 | Graham et al. |
| 2003/0017194 A1 | 1/2003 | Joerger et al. |
| 2003/0019813 A1 | 1/2003 | Ottersbach et al. |
| 2003/0022576 A1 | 1/2003 | Ottersbach et al. |
| 2003/0049437 A1 | 3/2003 | Devaney et al. |
| 2003/0068440 A1 | 4/2003 | Ottersbach et al. |
| 2005/0003163 A1 | 1/2005 | Krishnan |
| 2005/0065284 A1 | 3/2005 | Krishnan |

FOREIGN PATENT DOCUMENTS

| | | |
|---|---|---|
| DE | 3339662 A1 | 5/1984 |
| DE | 19833062 A1 | 2/2000 |
| EP | 0000426 A1 | 1/1979 |
| EP | 0239213 A2 | 9/1987 |
| EP | 286009 A2 | 10/1988 |
| EP | 0204312 B1 | 8/1990 |
| EP | 0469196 A1 | 2/1992 |
| EP | 0290676 B1 | 8/1994 |
| EP | 747456 A2 | 12/1996 |
| EP | 1109845 | 10/2005 |
| GB | 1299012 | 12/1972 |
| GB | 2091277 A | 7/1982 |
| NL | 7606306 | 12/1976 |
| WO | WO 91/12282 | 2/1991 |
| WO | WO 91/12282 | 8/1991 |
| WO | WO 97/15603 | 5/1997 |
| WO | WO 97/45468 | 12/1997 |
| WO | WO 98/51720 | 1/1998 |
| WO | WO 99/09837 | 3/1999 |
| WO | WO 00/05283 | 2/2000 |
| WO | WO 0008077 | 2/2000 |
| WO | PCT/US07/18838 | 2/2008 |
| WO | PCT/US07/018768 | 7/2008 |

OTHER PUBLICATIONS

Napper, "Steric Stabilization", J. Colloid Interface Sci., 58:2 390-407 (1977), Abstract: 86: 107053, XP002125110.

Ottewill et al., "Preparation of Core-Shell Polymer Colloid Particles by Encapsulation", Colloid & Polymer Science, pp. 274-283 (1997).

International Search Report, PCT/US99/17670, International Filing Date: Aug. 6, 1999.

"Polymer Compositions for Cationic Electrodepositable Coatings", Journal of Coatings Technology, Vo. 54, No. 686, Mar. 1982.

Rompp Chemie Lexikon (Chemical Dictionary), vol. 5, PI-S (1995), pp. 3558-3559.

Michelsen, T., "Building Materials (Survey)," *Kirk-Othmer Encyclopedia of Chemical Technology*, (1992 4th ed.), vol. 4, pp. 618-619.

ANTIMICROBIAL AND ANTISTATIC POLYMERS AND METHODS OF USING SUCH POLYMERS ON VARIOUS SUBSTRATES

RELATED APPLICATION

This application claims priority to U.S. Provisional Application Ser. No. 60/484,745, filed Jul. 3, 2003, the contents of which are hereby incorporated by reference as if recited in full herein.

FIELD AND BACKGROUND OF THE INVENTION

The present invention relates to polymers having inherent antimicrobial or antistatic properties. Such polymers can be applied or used in conjunction with a wide variety of substrates (e.g., textiles, metal, cellulosic materials, plastics, etc.) to provide the substrate with antimicrobial and/or antistatic properties. In addition, the polymers can also be combined with other polymers (e.g., the polymers of the invention can be used as additives) to provide such other polymers with antimicrobial and/or antistatic properties.

Various bacteria, fungi, viruses, algae and other microorganisms are known to be in the environment and to potentially adversely affect people coming in contact with them. Such microorganisms are often undesirable as a cause of illness, odors and damage to a wide variety of material and substrates. In order to combat such microorganisms, antimicrobial agents have been suggested. However, there is also a need for such agents to be both sustainable and to be compatible, and to be used on and with a wide variety of polymer materials and substrates.

Various additives and polymer systems have been suggested as providing antimicrobial properties. See, for example, U.S. Pat. No. 3,872,128 to Byck, U.S. Pat. No. 5,024,840 to Blakely et al, U.S. Pat. No. 5,290,894 to Malrose et al, U.S. Pat. Nos. 5,967,714, 6,203,856 and 6,248,811 to Ottersbach et al, U.S. Pat. No. 6,194,530 to Klasse et al. and U.S. Pat. No. 6,242,526 to Siddiqui et al.

With respect to antistatic properties, various substrates tend to accumulate static electrical charge due to low electrical conductivity. This is particularly problematic with plastic substrates. Such accumulation can adversely affect processing, cause electrical damage (e.g., in semiconductor devices), provide a fire hazard through the formation of an electrical arc, and exposes personnel handling the substrate to electrical shock. Various solutions to such static buildup have been suggested. See, for example, U.S. Pat. Nos. 4,029,694 and 4,093,676 to Weipert et al, U.S. Pat. No. 4,098,842 to Login, U.S. Pat. No. 4,857,590 to Gaggar et al. and U.S. Pat. No. 4,859,727 to Sasaki et al.

There, however, remains a need for potentially less toxic polymer compositions that provide sustainable antimicrobial and/or antistatic properties to a wide variety of substrates and materials.

SUMMARY OF THE INVENTION

The present invention relates to a substrate having antimicrobial and/or antistatic properties. Such properties are imparted by applying a coating or film formed from a cationically-charged polymer composition comprising a noncationic ethylenically unsaturated monomer, an ethylenically unsaturated monomer capable of providing a cationic charge to the polymer composition, and a steric stabilization component incorporated into the cationically-charged polymer composition.

The present invention also relates to a polymeric material comprising a base polymer blended with a cationically-charged polymer composition comprising a noncationic ethylenically unsaturated monomer, an ethylenically unsaturated cationic monomer capable of providing a cationic charge to the polymer composition, and a steric stabilization component incorporated into the cationically-charged polymer composition.

The present invention also relates to a method of providing antimicrobial and/or antistatic properties to a substrate. The method includes the step of applying the cationically-charged polymer composition described above to a substrate.

The present invention also relates to a method of imparting antimicrobial and/or antistatic properties to a polymer material. The method includes the step of blending a base polymer with the cationically-charged polymer composition described above.

DETAILED DESCRIPTION OF THE INVENTION

In the following detailed description, embodiments of the present invention are described in detail to enable practice of the invention. Although the invention is described with reference to these specific embodiments, it is understood that the invention is not limited to these embodiments. The invention includes numerous alternatives, modifications, and equivalents as will become apparent from consideration of the following detailed description.

As summarized above, the present invention utilizes a cationically-charged polymer composition to impart or provide antimicrobial and/or antistatic properties to a substrate or to be blended with a base polymer to provide a polymer material having antimicrobial and/or antistatic properties. The cationically-charged polymer composition includes a noncationic ethylenically unsaturated monomer an ethylenically unsaturated monomer capable of providing a cationic charge to the polymer composition, and a steric stabilization component.

Suitable substrates include, but are not limited to fabrics (both woven and non-woven), organic and inorganic particulates, fibers and agglomerates; foams; films; cellulosic material (e.g., paper or wood); metal; concrete; masonry; glass; and plastics, both thermoset and thermoplastic.

Various noncationic ethylenically unsaturated monomers may be used in the composition. Examples of monomers can be found in U.S. patent application Ser. No. 09/370,395 filed Aug. 6, 1999 and U.S. Pat. No. 5,830,934 to Krishnan, the disclosures of which are incorporated herein by reference in their entirety. Such monomers include, but are not limited to, vinyl aromatic monomers (e.g., styrene, para methyl styrene, chloromethyl styrene, vinyl toluene); olefins (e.g., ethylene); aliphatic conjugated diene monomers (e.g., butadiene); non-aromatic unsaturated mono- or dicarboxylic ester monomers (e.g., methyl methacrylate, ethyl acrylate, butyl acrylate, butyl methacrylate, glycidyl methacrylate, isodecyl acrylate, lauryl acrylate); monomers based on the half ester of an unsaturated dicarboxylic acid monomer (e.g., monomethyl maleate); unsaturated mono- or dicarboxylic acid monomers and derivatives thereof (e.g., itaconic acid); nitrogen-containing monomers (e.g., acrylonitrile, methacrylonitrile, acrylamide, methacrylamide, N-methylol acrylamide, N-(isobutoxymethyl) acrylamide); phosphorus-containing monomers; sulfur-containing monomers (e.g. styrene sulfonate); and vinyl ester monomers which includes branched vinyl esters (e.g., vinyl neodecanoate, vinyl versatates). Fluorinated analogs of alkyl acrylates or methacrylates may also be used. Mixtures of the above may be used.

The composition preferably comprises from about 20 to about 99 percent of the noncationic ethylenically unsaturated monomer based on the total monomer weight.

The composition also includes an ethylenically unsaturated cationic monomer capable of providing a cationic charge to the polymer composition. The cationic monomer is incorporated into the polymer composition by virtue of its ethylenic unsaturation. For the purposes of the invention, the term "cationic monomer" refers to any monomer which possesses or can be altered to provide a net positive charge. For example, this positive charge may be imparted by a heteroatom which is present in the monomer. Exemplary heteroatoms include, but are not limited to, nitrogen, sulfur, and phosphorus.

Examples of cationic monomers include amine and amide monomers, and quaternary amine monomers. Amine and amide monomers include, but are not limited to: dimethylaminoethyl acrylate; diethylaminoethyl acrylate; dimethyl aminoethyl methacrylate; diethylaminoethyl methacrylate; tertiary butylaminoethyl methacrylate; N,N-dimethyl acrylamide; N,N-dimethylaminopropyl acrylamide; acryloyl morpholine; N-isopropyl acrylamide; N,N-diethyl acrylamide; dimethyl aminoethyl vinyl ether; 2-methyl-1-vinyl imidazole; N,N-dimethylaminopropyl methacrylamide; vinyl pyridine; vinyl benzyl amine methyl chloride quarternary; dimethylaminoethyl methacrylate methyl chloride quaternary; diallyldimethylammonium chloride; N,N-dimethylaminopropyl acrylamide methyl chloride quaternary; trimethyl-(vinyloxyethyl) ammonium chloride; 1-vinyl-2,3-dimethylimidazolinium chloride; vinyl benzyl amine hydrochloride; vinyl pyridinium hydrochloride; and mixtures thereof.

Quaternary amine monomers which may be used in the composition of the invention can include those obtained from the above amine monomers such as by protonation using an acid or via an alkylation reaction using an alkyl halide.

Alternatively, the ethylenically unsaturated monomer capable of providing a cationic charge comprises a quaternary derivative capable of providing hydrophobicity. In a preferred embodiment, the quaternary derivative is based on an alkyl group having two to twenty carbons ($C_2$ to $C_{20}$). For example, one could use:

1. $CH_2=C(R)COOCH(OH)CH_2N^+(X^-)(R')$ where R=H, $CH_3$ and $R'=(CH_2)_nCH_3$ or $(CF_2)CF_3$ and X=Cl, Br, I or a sulfate. For example, this could be a reaction product of glycidyl methacrylate and a secondary amine which has then been quaternized 2. $CH_2=C(R)\Phi CH_2N^+(X^-)(R')$ where R, R' and X have the same significance as above. This is a similar reaction as compared to the one above with vinyl benzyl chloride as the starting material.

3. The third approach could be to start with vinyl pyridine and make the alkyl pyridinium salts as above.

Amine salts can also be used and are obtained, for example, by the reaction of an epoxy group with a secondary amine and subsequent neutralization of the newly formed tertiary amine with an acid. An example of this is the reaction product of glycidyl methacrylate with a secondary amine that can be free radically polymerized. Quaternary amine functionality can also be generated as a post reaction on a preformed polymer having, for example, an epoxy group. Examples of these kinds of reactions are described in the article, "Polymer Compositions for Cationic Electrodepositable Coatings, *Journal of Coatings Technology*, Vol 54, No 686, March 1982. It should also be appreciated that cationic functionality can also be imparted via sulfonium or phosphonium chemistry, examples of which are also described in the above article.

The composition preferably comprises from about 0.5 to about 75 percent of the ethylenically unsaturated monomer capable of providing a cationic charge based on the total monomer weight, the amount depending on the selected application of the polymer composition.

The composition also comprises a component which is incorporated into the cationically-charged polymer composition to sterically stabilize the composition. Suitable components include, but are not limited to, monomers, polymers, and mixtures thereof as set forth below. For the purposes of the invention, the term "incorporated" with respect to the use of the monomer can be interpreted to mean that the monomer attaches to the backbone of the cationic polymer. The polymer which is "incorporated" into the composition can be interpreted to mean that it is adsorbed or grafted onto the composition surface, an example of which may be polyvinyl alcohol. This stabilizing component may encompass a nonionic monomer or polymer which incorporates steric stabilization to the composition particle without adversely affecting the polymer composition. Exemplary monomers that can be used as steric stabilizers include, but are not limited to, those which contain alkoxylated (e.g., ethoxylated or propoxylated) functionality. Examples of such monomers include those described by the formulas:

$CH_2=C(R)COO(CH_2CHR'O)_nR''$—where R=H, $C_1$-$C_4$ alkyl; and R'=H, $C_1$-$C_4$ alkyl, and R''=H, $C_1$-$C_{12}$ alkyl, and n=1-30; or $CH_2=C(R)COO(CH_2CH_2O)_n(CH_2CHR'O)_mR''$—where R=H, $C_1$-$C_4$ alkyl, and R'=H, $C_1$-$C_4$ alkyl, and R''=H, $C_1$-$C_{12}$ alkyl, n and m each may range from 1-15; and $CH_2=C(R)COO(CH_2CHR'O)_n(CH_2CH_2O)_mR''$—where R=H, $C_1$-$C_4$ alkyl, and R'=H, $C_1$-$C_4$ alkyl and R''=H, $C_1$-$C_{12}$ alkyl, n and m=1-15.

Preferred compounds are undecylenic acid esters where R'' is $C_{11}$. Preferably, the monomers have a molecular weight of less than 2000.

Ethoxylated mono- and diesters of diacids such as maleic and itaconic acids can also be used to achieve the same stabilizing effect.

Polymerizable surfactants based on acrylate, methacrylate, vinyl and allyl versions of surfactants can also be used. An example of this is TREM LF-40 sold by Henkel of Düsseldorf, Germany. These surfactants possess ethylenic unsaturation that allows the surfactants to be incorporated into the polymer composition. Similar to other surfactants, these materials have hydrophobic and hydrophilic functionality that varies. Surfactants that are particularly applicable to the present invention are nonionic surfactants wherein the hydrophilic character is believed to be attributable to the presence of alkylene oxide groups (e.g., ethylene oxide, propylene oxide, butylene oxide, and the like). Block copolymers of ethylene oxide and/or propylene oxide such as the Pluronic or Tetronic series from BASF can also be used, particularly in antistatic applications. The degree of hydrophilicity can vary based on the selection of functionality.

Polymers can also be used to provide steric stability. For example, protective colloids may be used. Examples of these materials include, but are not limited to, polyvinyl alcohols, polyvinyl pyrollidone, hydroxyethyl cellulose, polyethylene glycols, polyglycol-ethers, propylene glycols, ethylene oxide/propylene oxide copolymers, ethylene oxide/propylene oxide copolymers and/or ethylene oxide/butylene oxide copolymers and the like. Mixtures of any of the above monomers and polymers may also be used. Other monomers and polymers which may be used to impart stability are listed in U.S. Pat. No. 5,830,934 to Krishnan et al.

The steric stabilization component which is used to stabilize the composition is present in an amount ranging from about 0.5 to about 75 percent based on the total weight of the monomers.

The composition of the invention also may include a free radical initiator, the selection of which is known in the art. Preferably, a free radical initiator is used which generates a cationic species upon decomposition and contributes to the cationic charge of the composition. An example of such an initiator is 2,2'-azobis(2-amidinopropane) dihydrochloride) sold commercially as Wako V-50 by Wako Chemicals of Richmond, Va.

The composition of the invention may also include other additives to improve the physical and/or mechanical properties of the polymer, the selection of which are known to one skilled in the art. These additives include processing aids and performance aids such as, but are not limited to, crosslinking agents, natural and synthetic binders, plasticizers, softeners, foam-inhibiting agents, froth aids, flame retardants, dispersing agents, pH-adjusting components, sequestering or chelating agents, and other components. In a preferred embodiment 0.1 to 1.0 weight percent of a nonionic surfactant can be used. Additionally, the composition preferably is devoid of conventional non-polymerizable cationic and anionic surfactants.

The composition may be applied to the substrate as a coating or film using techniques known to those skilled in the art such as spraying, roll-coating, brushing, dipping, impregnation, size press and the like.

The composition of the present invention can be blended with a base polymer including other polymers. Suitable polymers include various thermoplastic and thermosetting polymers including, but not limited to polyurethanes, phenolics, polyesters, polyolefins, polyamides, polycarbonates, polyethers, polyether-amides and imides, polyorganosilanes, polysulfones, polyisoprene, polychloroprene, acrylics, styrene-butadienes, styrene acrylonitriles, ABS, EVA, polytetrafluoroethylene, polyether-esters, polyepoxides, heterocyclic polymers such as polypyrrole, polyaniline, polythiophene and its derivatives and the like and latex-based materials. In another embodiment, the cationically-charged polymer can be blended with another polymer having antimicrobial or antistatic properties such as other cationic polymers.

The blends could be made in situ creating an interpenetrating polymer network (IPN). Core shell latices or composites could be made that have one or more of these above mentioned components as a core on which subsequent polymerization could take place by an emulsion or suspension process. Another example of this would be making the polymers, e.g., urethanes, starting from the base raw materials by a suspension or dispersion/miniemulsion process followed by a radical process. Thus one could combine a condensation and a free radical process together. The objective would be to make a broader range of polymers that are hybrids. Another enhancement of the chemistry could come from using controlled radical polymerization processes such as RAFT, ATRP, and SFRP (with nitroxides) which would then provide polymers that would have a variety of architectures such as block, graft, stars, hyperbranched and dendrimers. This allows control of the morphology, activity, and uniqueness of the polymers and enables one to create molecules tailored to meet specific functions.

The composition can be used in the form of an open or closed cell foam by adding surfactants and foaming agents. The foam can be used in a wide variety of ways so as to impart antimicrobial and/or antistatic properties to various articles. For example, a foam could be used to provide both sound deadening properties and antimicrobial/antistatic properties to an article like the foam underlay of a carpet. The foam could be used as the article itself, for example, the foam of a pillow or mattress. The foam could be used as an absorbent in a diaper thereby absorbing the urine while providing antimicrobial protection.

Amphoteric or zwitterionic polymers in which an anionic polymer would be included could also be made using the composition of the present invention.

Antimicrobial and/or antistatic agents may be used as an additive to enhance the inherent antimicrobial or antistatic nature of the compositions of the present invention. A potential antimicrobial monomer is undecylenic acid or alcohol or reaction products of undecylenic acid or alcohol with hydroxyl or acid containing materials having ethylenic unsaturation to produce an ester. An example of the acid functional monomer is acrylic acid or maleic anhydride. An example of the hydroxyl functional monomer is hydroxylethyl methacrylate or polyethylene glycol methacrylate. Undecylenic acid is known to provide antifungal properties and this could potentially offer advantages again in expanding the chemistry especially if combined with the cationic and phenolic type intermediates.

Chitosan, modified chitosans or chitosan salts can also be incorporated into the composition. Chitosan is a naturally occurring amino functional saccharide which is known to be antimicrobial. Moreover, chitosan could also serve the dual purpose of also providing steric stabilization.

Other antimicrobial agents include metal biocides such as silver, zinc, etc. and salts and oxides thereof, chlorhexidine, chlorhexidine gluconate, glutaral, halazone, hexachlorophene, nitrofurazone, nitromersol, povidone-iodine, thimerosol, $C_1$-$C_5$-parabens, hypochlorite salts, clofucarban, clorophene, poloxamer-iodine, phenolics, mafenide acetate, aminacrine hydrochloride, quaternary ammonium salts, oxychlorosene, metabromsalan, merbromin, dibromsalan, glyceryl laurate, sodium and/or zinc pyrithione, (dodecyl) (diethylenediamine) glycine and/or (dodecyl) (aminopropyl) glycine; phenolic compounds (e.g., phenols, m-cresol, n-cresol, p-cresol, o-phenyl-phenol, resorcinol, vinyl phenol, etc.), polymeric guanidines, quaternary ammonium salts, polymyxins, bacitracin, circulin, the octapeptins, lysozmye, lysostaphin, cellulytic enzymes generally, vancomycin, ristocetin, the actinoidins and avoparcins, tyrocidin A, gramicidin S, polyoxin D, tunicamycin, neomycin, streptomycin and the like. It is not feasible to give here an exhaustive list of potentially useful antimicrobials, but this may be found in compendia such as, "Antibiotics, Chemotherapeutics, and Antibacterial Agents for Disease Control," M. Grayson, Ed., J. Wiley and Sons, N.Y., 1982. Classification of antibiotics by their mode of action may be found in "The Molecular Basis of antibiotic Action," Second Edition, E. F. Gale et al., J. Wiley and sons, N.Y., 1981. Other additives and polymer systems are described in U.S. Pat. No. 3,872,128 to Byck, U.S. Pat. No. 5,024,840 to Blakely et al, U.S. Pat. No. 5,290,894 to Malrose et al, U.S. Pat. Nos. 5,967,714, 6,203,856 and 6,248,811 to Ottersbach et al, U.S. Pat. No. 6,194,530 to Klasse et al. and U.S. Pat. No. 6,242,526 to Siddiqui et al., the disclosures of which are incorporated by reference in their entirety.

Antistatic agents include nitrogen compounds such as long chain amines, amides and quaternary ammonium salts, esters of fatty acids and their derivatives, polyhydric alcohols and their derivatives, phosphoric acid derivatives, solutions of electrolytes in liquids with high dielectric constants, metallic salts and oxides, metals (e.g., iron), carbon black, carbon nanotubes and semiconductors. Specific examples include Hostenstat® and Sandin® antistats from Clariant, Larostat® antistats from BASF, Bayhydrol® antistats from Bayer, Atmer® antistats from Uniquema, VersaTL® from Alco, and various other antistats offered by Atofina, Noveon, Ciba, Eastman, Agfa, Ormecon Chemie and Panipol.

With respect to providing antistatic compositions, the reaction products of alkyl amines or ethoxylated amines with maleic anhydride could also be used. This could lead to a maleimide-type monomer with ethoxylate or alkyl chains that could be copolymerized with other monomers. Copolymers of alkylene oxide macromers and other monomers such as styrene sulfonates, acrylamidopropane sulfonic acid (AMPS) carboxylic acids, (e.g., acrylic or methacrylic derivatives) are potential antistatic additives. Other antistatic solutions are suggested in U.S. Pat. Nos. 4,029,694 and 4,093,676 to Weipert et al, U.S. Pat. No. 4,098,842 to Login, U.S. Pat. No. 4,857,590 to Gaggar et al. and U.S. Pat. No. 4,859,727 to Sasaki et al., the disclosures of which are incorporated by reference in their entirety.

The cationically-charged polymer composition could also be used as an additive in the solid form to be added to specific substrates and then processed. In the case where the solid is to be used it would be added to the base polymer during the processing stage, e.g., as pellets into polycarbonate or SAN before extrusion or injection molding. In this case, the composition of our invention would become the integral part of the article as opposed to a topical coating on the surface. The polymers can be made in the solid form either by spray drying a dispersion/emulsion or by making it directly as a solid by suspension polymerization.

It is possible to conceive ways by which the composition of our invention can be directly incorporated into a fiber while it is being processed. One way is during the melt spinning/extrusion of the fibers. The additive could be added directly to the polymer used for fiber making e.g., polyolefins, polyester, acrylic etc during the processing stage or could be pre-compounded into a master batch with the polymer and other ingredients and mixed thoroughly before addition to the fiber making polymer. This way the composition is mixed thoroughly before addition to the fiber making polymer. This way the composition would be directly extruded or be part of the fiber and impart its antimicrobial or antistatic properties. This would apply to any polymer that can be melt spun and the additive can be designed to impart compatibility, hydrophilicity, flexibility etc to the fiber in addition to the stated properties for which it was designed. These fibers then could be used for many applications some of which have been outlined above. Solution spinning of fibers could also be considered in which case the additive would be dissolved in the fiber spinning solution and then extruded through spinnerets.

Another area which would benefit from the solid additive processing is plastics and rubber articles. Here again one could conceive of adding the composition polymer (which would serve as a thermoplastic additive) as powder or pellets directly during the processing step such as extrusion, injection molding etc or could be pelletized prior to actually processing in a compatibilizing polymer such as EVA and EMA using the extruder and added to any thermoplastic polymer in specific amounts during a post processing step using the extruder, injection molding machine, blow molding, etc. Typical plastic processing steps for thermoplastic polymers would be compatible with these solid additives. Also, the additive can be mixed along with other ingredients such as pigments, flow aids, lubricants etc, and the desired polymer to make what are known as master batches. These master batches would typically be made in high shear mixing equipment such as a Banbury mixer and the mix would then be pelletized in an extruder. The master batches would then be processed by the manufacturer of plastic articles or films using conventional plastic processing equipment. Any or all of the above methods could be used to deliver the additive into a matrix polymer for providing the desired antimicrobial and/or antistatic property. Once again the applications would be similar to the ones outlined above. The dry polymer could be added to thermoset polymer also e.g. phenolics, epoxies etc and processed using techniques such as compression molding etc. the additive processing techniques for rubber would be similar in terms of making a rubber compound using a Banbury and then made into sheets, for example through a two roll mill or extruded into tubes, pipes, hoses etc.

One specific application could be in the area of artificial or synthetic marble surfaces made of acrylic polymers e.g., Corian® or unsaturated polyesters. The polymer additive could be compounded into these resins and then cast or cured to incorporate it into the matrix. This would permanently incorporate the additive into the matrix instead of a topical coating. The same could be for the use of these additives in gel coats and casting resins used in boats etc to provide surfaces with the described properties. If an unsaturated polyester resin were used, it would be preferable to dissolve the additive in styrene Another example for solids would be use of these as additives in hot melt adhesive compositions to create adhesives that have the described attributes. The polymer would have to have the required compatibility and molecular weight to provide adequate flow.

In the case of cellulosic materials, the use of solid materials can be envisaged in composites made from wood where the wood in granular, pelletized or powder form could be compounded with other ingredients and then molded into a shape by techniques such as compression molding. Thermosetting resins such as UF, MF, epoxy and urethane resins are used for bonding wood and the polymer composition could be added along with these during the processing stage. Applications such as decking and construction materials and OSB boards could be considered using this approach.

The use of solid material in paper can be considered in the making of high-pressure laminate or decorative laminates and molded articles. Once again the solid material can be combined with pulp fibers and fillers and compression molded to make the finished product. Packaging materials such as cartons, boxes, etc could also benefit from the practice of the present invention.

The cationically-charged polymer composition in dry form can be combined with cement/concrete and set to form a concrete structure that has the desired addendum properties. Grouts, sealers, mastics etc would also be amenable to the use of powders. This can also be combined with other fillers etc to make granite counter tops, floors etc that have antimicrobial-antistatic properties. Redispersible powders in cement would be another use and in decorative concrete.

The composition of the present invention should also be used in combination with other methods and formulations for improving antimicrobial and/or antistatic properties such as described in U.S. Pat. No. 3,872,128 to Byck, U.S. Pat. No. 5,024,840 to Blakely et al, U.S. Pat. No. 5,290,894 to Malrose et al, U.S. Pat. Nos. 5,967,714, 6,203,856 and 6,248,811 to Ottersbach et al, U.S. Pat. No. 6,194,530 to Klasse et al., U.S. Pat. No. 6,242,526 to Siddiqui et al., U.S. Pat. Nos. 4,029,694 and 4,093,676 to Weipert et al, U.S. Pat. No. 4,098,842 to Login, U.S. Pat. No. 4,857,590 to Gaggar et al., and U.S. Pat. No. 4,859,727 to Sasaki et al.

Potential Uses

The composition of the present invention can be applied to a wide variety of substrates using various techniques known to those skilled in the art. The following list is not to be intended as limiting the types of substrates. For example, the composition as a latex can be applied as a coating or as a film to the following substrates:

1. Nonwoven and Woven Textiles and Fibers: Examples would include natural fibers such as cotton and wool to synthetic fibers such as nylon, acrylics, polyesters, urethanes etc. Application process would be through processes such as rod/knife coating, impregnation, back coatings, printing or as pretreatments on individual fibers or as a finished good.

2. Plastics/Rubber: Examples would include commodity molded thermoplastics like polyolefins to engineering thermoplastics such as polysulfones, acetals, polycarbonates etc., thermosets like epoxies, urethanes etc and as extruded or blown films. The polymer would be applied as a coating on the surface by rod/knife coating, spray, dipping or as a laminate coating during the extrusion process or as a coating applied in the mold during the molding process. Rubber products would include sheets, extruded/molded articles, composites etc.

3. Paper: This would include both preformed paper and as additives in the wet end process. Typical paper processes would include impregnation or saturation, rod/knife coating etc, size press, and wet end addition, spray-on.

4. Inorganic/Organic Materials: This would cover a wide range of delivery mechanisms based on encapsulation and coating of inorganic particles e.g., clay, mica, pigments, biocides, pesticides, etc. . . . , and also as part of a formulation involving a variety of fillers to make a finished product e.g., gypsum board, sealer, grout etc., or as a coating on an inorganic surface such as a drywall, tiles, applied by spraying, roller coating, brushing etc. This would also cover its use in glass fiber mat coating or impregnation.

5. Wood: This would include all kinds of wood substrates both natural and engineered and the application process could be a variety of methods as outlined above.

6. Metal: Again this would encompass both metals and metal alloys, e.g., carbon steel, stainless steel and including solid steel bars, sheets, coils, ropes etc wherein the composition is applied as a coating by one of the numerous processes such as spraying dipping, brushing, roller coating etc.

Specific applications include textiles such as: residential and commercial carpets, tiles, etc.; liquid and air filters—HVAC, vacuum cleaners, automotive; medical surgical gowns, drapes, dressings, covers etc.; pretreatment for fibers, printed and dyed fabrics for apparel, furnishings, sheets, towels etc.; diapers and incontinence articles, interior automotive applications such as trim, upholstery, mats, filters, etc.; upholstery coatings, laminating and bonding adhesives; foams for sound absorbency; foamed articles such as pillows and mattresses; belting—food handling etc.; tapes—masking tapes, surgical, industrial tapes e.g., electrical, industrial and household cleaning wipes, cloths and sponges; shoe products e.g., insoles, box toes, etc.; plastics/rubber such as tool handles—e.g., screw drivers, shovels, etc.; toys, rubber gloves, sheets, articles; machinery housing—e.g., computers, display and diagnostic devices, vacuum cleaners, instrumentation; medical devices—e.g., catheters, balloons, tubing, syringes, diagnostic kits etc.; packaging/product protection—perishables, computer peripherals, semiconductors, memory chips, CD's, DVD's etc.; impact modifiers for acrylics, polycarbonates etc.; overdips and underdips for gloves—gloves for clean room, breathable films, antipenetrant for fabric supported gloves; cutting boards; extruded and blown films for packaging; paper: vacuum bags, book covers, air filters, liquid filters, wallcoverings, wet and dry wipes, tissues, etc.; felt for vinyl floor coverings, molded pulp applications, packaging—boxes, cartons, molded articles etc.; size press coatings—gift wraps, ink jet media, breathable coatings, etc.; wet end additives in paper, tapes and labels—masking, surgical, general purpose etc.; adhesives—tapes, labels, decals, films, book binding, pressure sensitive and FPLA, etc.; shoe insoles, inorganic/organic materials such as coating/encapsulation of fillers and pigments, construction sealers and grouts, gypsum wallboard coatings/paints, exterior/interior coatings; tile adhesives, floor coatings—hospitals, clean rooms, clinics, schools etc.; coatings for hospital and medical environments; ceiling tiles, glass fiber coating—glass mats, insulation, reinforced composites etc.; liquid disinfectants and cleaners, personal care—shampoos, lotions, creams, hair and skin care, body wash, cosmetics etc.; hygiene coatings of surfaces other than floors—hospitals, clinics, schools, homes and offices, hard and porous surface coatings—walls, ceilings, floors, counter tops etc.; decorative concrete, wood such as oriented strand board (OSB) coatings, decking and construction materials—coating, impregnation etc.; composite construction materials, furniture coatings; hygiene coatings—table and counter tops, door knobs, door handles etc.; flooring—laminates, hardwood and other composite floors, decorative laminates—table tops, counter tops, furniture etc.; metal such as cabinets, door knobs, handles etc.; furniture, coatings—appliances, OEM etc.

Having generally described the present invention, a further understanding can be obtained by reference to the examples provided herein for purposes of illustration only and are not intended to be limiting.

EXAMPLES

Examples 1-4 were tested for antimicrobial properties using *Bacillus subtilis* ATCC #6633 as the test organism. Example 3 is an anionic polymer and is a comparative example.

|  | 1 | 2 | 3 | 4 |
|---|---|---|---|---|
| Monomer Composition | | | | |
| Styrene | 54.5 | 47.5 | 55 | 39.5 |
| Butyl acrylate | 13.5 | 13.5 | 0 | 28.5 |
| Butadiene | 20.0 | 20.0 | 43 | 0 |
| Lauryl Methacrylate | 0 | 0 | 0 | 10.0 |
| N-methylolacrylamide | 2.0 | 2.0 | 0 | 2.0 |
| Dimethyl aminoethyl methacrylate methyl chloride quaternary | 5.0 | 12.0 | 0 | 15.0 |
| Monomethyl maleate | | | 2.0 | 0 |
| Surfactants | | | | |
| Abex 2525 | 0.5 | 0.5 | 0.0 | 0.5 |
| Methoxyl polyethylene glycol methacrylate | 5.0 | 5.0 | 0.0 | 5.0 |
| Dowfax 2A1 | | | 1.2 | |

Quanticult® Plus cultures containing 10-100 CFU/0.1 mL were inoculated and allowed to dry onto fifteen coupons for each test coating. Fifteen coupons coated with the negative control coating were inoculated in the same manner. Recovery for each surface type was determined after one hour, four hours and 24 hours, using Rodac plates (TSA containing Tween and Lecithin). At each sample time a Rodac plate was touched to five coupons for each surface type and incubated at 30-35° C. for 48 hrs-5 days. The CFU were counted and averaged for each surface type. The test surface results were compared with the negative control surface results. Recovery <70% indicates that the material is antimicrobial. The results are provided in Tables 1-4.

TABLE 1

(Example 1)
Microbial Recovery

| Replicate | 1 Hour | | 4 Hour | | 24 Hour | |
|---|---|---|---|---|---|---|
| | B. subtilis CFU | Other CFU | B. subtilis CFU | Other CFU | B. subtilis CFU | Other CFU |
| 1 | 0 | 2 | 0 | 4 | 0 | 6 |
| 2 | 0 | 9 | 0 | 9 | 0 | 4 |
| 3 | 0 | 20 | 0 | 2 | 0 | 9 |
| 4 | 0 | 24 | 0 | 7 | 0 | 7 |
| 5 | 0 | 31 | 0 | 6 | 0 | 3 |
| Average | 0 | N/A | 0 | N/A | 0 | N/A |
| % Recovery[1,2] | | | | | | |
| N/A | 0 | | 0 | | 0 | |

[1]Percent Recovery calculated using only the B. subtilis CFUs.
[2]Percent Recovery calculated by comparing the average CFU to those of Example 3.

TABLE 2

(Example 2)

| Replicate | 1 Hour | | 4 Hour | | 24 Hour | |
|---|---|---|---|---|---|---|
| | B. subtilis CFU | Other CFU | B. subtilis CFU | Other CFU | B. subtilis CFU | Other CFU |
| 1 | 0 | 0 | 0 | 1 | 0 | 1 |
| 2 | 0 | 0 | 0 | 1 | 0 | 3 |
| 3 | 0 | 0 | 0 | 2 | 0 | 4 |
| 4 | 0 | 0 | 0 | 0 | 0 | 5 |
| 5 | 0 | 1 | 0 | 0 | 0 | 3 |
| Average | 0 | N/A | 0 | N/A | 0 | N/A |
| % Recovery[1,2] | | | | | | |
| N/A | 0 | | 0 | | 0 | |

[1]Percent Recovery calculated using only the B. subtilis CFUs.
[2]Percent Recovery calculated by comparing the average CFU to those of Example 3.

TABLE 3

(Comparative Example 3)

| Replicate | 1 Hour | | 4 Hour | | 24 Hour | |
|---|---|---|---|---|---|---|
| | B. subtilis CFU | Other CFU | B. subtilis CFU | Other CFU | B. subtilis CFU | Other CFU |
| 1 | 1 | 4 | 7 | 12 | 4 | 13 |
| 2 | 3 | 5 | 6 | 2 | 0 | 10 |
| 3 | 2 | 2 | 5 | 5 | 0 | 9 |
| 4 | 2 | 3 | 1 | 8 | 0 | 15 |
| 5 | 2 | 2 | 9 | 11 | 2 | 6 |
| Average | 2 | N/A | 5.6 | N/A | 1.2 | N/A |

[1]% Recovery calculated using only the B. subtilis CFUs.

TABLE 4

(Example 4)

| Replicate | 1 Hour | | 4 Hour | | 24 Hour | |
|---|---|---|---|---|---|---|
| | B. subtilis CFU | Other CFU | B. subtilis CFU | Other CFU | B. subtilis CFU | Other CFU |
| 1 | 0 | 0 | 0 | 2 | 0 | 0 |
| 2 | 0 | 0 | 0 | 0 | 0 | 2 |
| 3 | 0 | 0 | 1 | 1 | 0 | 1 |
| 4 | 1 | 0 | 0 | 0 | 0 | 1 |
| 5 | 0 | 0 | 0 | 0 | 0 | 3 |
| Average | 0.2 | N/A | 0.2 | N/A | 0 | N/A |
| % Recovery[1,2] | | | | | | |
| N/A | 10 | | 10 | | 0 | |

[1]Percent Recovery calculated using only the B. subtilis CFUs.
[2]Percent Recovery calculated by comparing the average CFU to those of Example 3.

This demonstrates that the compositions of the present invention provide rapid kill of bacteria and also are effective as a broad spectrum antimicrobial polymer composition as compared to comparative example, Example 3.

The compositions of Examples 1, 2 and 4 were coated onto paper. The average charge decay time was determined by measuring the length of time for charge to decay to 10 percent of its value when the object is grounded. In operation, the object is charged using a dc voltage service and the drop in voltage is measured after grounding. The surface resistivity is measured by placing two electrodes on the surface and applying a fixed voltage to one electrode. The current that traveled across the surface to the other electrode is measured. Resistance then can be measured from the current and applied voltage. The results are provided in Table 5.

TABLE 5

(Antistatic Properties-Coated Free Sheet)

| | Uncoated Paper | | Example 1 | | | | Example 2 | | | | Example 4 | | | |
|---|---|---|---|---|---|---|---|---|---|---|---|---|---|---|
| Polymer add-on (lbs/3000 sq ft) | — | | 5.0 | | 10.0 | | 5.0 | | 10.0 | | 5.0 | | 10.0 | |
| Relative Humidity (%) | 12 | 55 | 12 | 55 | 12 | 55 | 12 | 55 | 12 | 55 | 12 | 55 | 12 | 55 |
| Avg. Charge Decay | 54.8 | 0.17 | 8.9 | 0.02 | 8.0 | 0.04 | 0.87 | 0.01 | 0.02 | 0.01 | 0.01 | 0.01 | 0.01 | 0.01 |

TABLE 5-continued (Antistatic Properties-Coated Free Sheet)

| | Uncoated Paper | | Example 1 | | | | | Example 2 | | | | Example 4 | |
|---|---|---|---|---|---|---|---|---|---|---|---|---|---|
| Time(s) Surface Resistivity (ohms/sq. @ 10 V) | >E12 | 3.4E+11 | >E12 | 2.5E+11 | >E12 | 2.1+11 | 2.2E+12 | 3.8E+09 | 6.6E+10 | 1.0E+08 | 9.0E+10 | 1.3E+08 | 1.1E+10 | 3.1E+07 |

This illustrates that antistatic properties are imparted by the composition of the present invention.

In the specification, there have been disclosed typical embodiments of the invention and, although specific terms are employed, they are used in a generic and descriptive sense only and not for purposes of limitation. The following claims are provided to ensure that the present application meets all statutory requirements as a priority application in all jurisdictions and shall not be construed as setting forth the full scope of the present invention.

The invention claimed is:

1. A cationically-charged polymer composition comprising:
   a noncationic ethylenically unsaturated monomer,
   an ethylenically unsaturated monomer capable of providing a cationic charge to the polymer composition,
   a steric stabilization component incorporated into the cationically-charged polymer composition, wherein the steric stabilization component is a polymerizable surfactant, a monomer having alkoxylated functionality, or a protective colloid, and
   an antimicrobial agent further comprising undecylenic acid or alcohol or a reaction product of undecylenic acid with hydroxyl or acid containing material having ethylenic unsaturation.

2. A substrate having applied thereto a coating or film to provide antimicrobial and/or antistatic properties, said coating or film formed from a cationically-charged polymer composition consisting essentially of about 20 to about 99 weight percent of a noncationic ethylenically unsaturated monomer, about 0.5 to about 75 weight percent of an ethylenically unsaturated monomer capable of providing a cationic charge to the polymer composition, about 0.5 to about 75 weight percent of a steric stabilization monomer, and 0 to 1.0 weight percent of a nonionic surfactant, wherein cationically-charged polymer composition is devoid of cationic and anionic surfactants.

3. The substrate according to claim 2, wherein the substrate is selected from the group consisting of non-woven and woven fabrics; organic and inorganic particulates, fibers and agglomerates; foams; films, cellulosic materials; concrete, masonry; glass; metal; and plastic.

4. The substrate according to claim 2, wherein the noncationic ethylenically unsaturated monomer is selected from the group consisting of vinyl aromatic monomers; olefins; aliphatic conjugated diene monomers; non-aromatic unsaturated mono- or dicarboxylic ester monomers; monomers based on the half ester of an unsaturated dicarboxylic acid monomer; unsaturated mono- or dicarboxylic acid monomers and derivatives thereof; nitrogen-containing monomers; phosphorous-containing monomers; sulfur-containing monomers; and vinyl ester monomers.

5. The substrate according to claim 2, wherein the ethylenically unsaturated monomer capable of providing a cationic charge to the polymer composition comprises an amine or amide monomer.

6. The substrate according to claim 2, wherein the ethylenically unsaturated monomer capable of providing a cationic charge to the polymer composition comprises a quaternized amine monomer.

7. The substrate according to claim 2, wherein the ethylenically unsaturated monomer capable of providing a cationic charge to the polymer composition comprises a quaternary derivative capable of providing hydrophobicity to the polymer composition, wherein the quaternary derivative is an ethylenically unsaturated monomer that comprises a quaternary ammonium salt, and wherein the quaternary ammonium salt comprises one or more alkyl groups having two to twenty carbons.

8. The substrate according to claim 2, wherein the steric stabilization component is a monomer having alkoxylated functionality or is a protective colloid.

9. The substrate according to claim 8, wherein the monomer having alkoxylated functionality is selected from the group consisting of:
   (a) $CH_2=C(R)COO(CH_2CHR'O)_nR''$, where R is H or $C_1$-$C_4$ alkyl; R' is H or $C_1$-$C_4$ alkyl; R'' is H or $C_1$-$C_{12}$ alkyl; and n is 1-30;
   (b) $CH_2=C(R)COO(CH_2CH_2O)_n(CH_2CHR'O)_mR''$, where R is H or $C_1$-$C_4$ alkyl; R' is H or $C_1$-$C_4$ alkyl; R'' is H or $C_1$-$C_{12}$ alkyl; and n and m each is 1-15;
   (c) $CH_2=C(R)COO(CH_2CHR'O)_n(CH_2CH_2O)_mR''$, where R is H or $C_1$-$C_4$ alkyl; R' is H or $C_1$-$C_4$ alkyl; R'' is H or $C_1$-$C_{12}$ alkyl; and n and m each is 1-15; and
   (d) mixtures of (a) and (b).

10. The substrate according to claim 2, wherein the steric stabilization component is a polymerizable surfactant.

11. The substrate according to claim 2, wherein the polymer composition further includes an antimicrobial agent or antistatic agent.

12. The substrate according to claim 11, wherein the antimicrobial agent is a chitosan-based material.

13. The substrate according to claim 11, wherein the antimicrobial agent is a metal biocide selected from the group consisting of silver and zinc, and salts and oxides thereof.

14. The substrate according to claim 11, wherein the antistatic agent is selected from the group consisting of nitrogen compounds, esters of fatty acids, polyhydric alcohols, solutions of electrolytes in liquids with high dielectric constants, metallic salts and oxides, metals, carbon black, carbon nanotubes and semiconductors.

15. The substrate according to claim 11, wherein the antimicrobial agent is undecylenic acid or alcohol or a reaction product of undecylenic acid with hydroxyl or acid containing material having ethylenic unsaturation.

16. A foam having antimicrobial and/or antistatic properties, said foam comprising:
a base polymer blended with a cationically-charged polymer composition comprising
a noncationic ethylenically unsaturated monomer,
an ethylenically unsaturated monomer capable of providing a cationic charge to the polymer composition, and
a steric stabilization component incorporated into the cationically-charged polymer composition, wherein the steric stabilization component is a polymerizable surfactant, a monomer having alkoxylated functionality or a protective colloid.

17. The foam according to claim 16, wherein said base polymer is selected from the group consisting of polyurethanes, phenolics, polyesters, polyolefins, polyamides, polycarbonates, polyethers, polyether-amides, polyether-imides, polyorganosilanes, polysulfones, polyisoprene, polychloroprene, acrylics, styrene-butadienes, styrene acrylonitriles, ABS, EVA, polytetrafluoroethylene, polyether-esters, and polyepoxides.

18. The foam according to claim 16, wherein the noncationic ethylenically unsaturated monomer is selected from the group consisting of vinyl aromatic monomers; olefins; aliphatic conjugated diene monomers; non-aromatic unsaturated mono- or dicarboxylic ester monomers; monomers based on the half ester of an unsaturated dicarboxylic acid monomer; unsaturated mono- or dicarboxylic acid monomers and derivatives thereof; nitrogen-containing monomers; phosphorous-containing monomers; sulfur-containing monomers; and vinyl ester monomers.

19. The foam according to claim 16, wherein the ethylenically unsaturated monomer capable of providing a cationic charge to the polymer composition comprises an amine or amide monomer.

20. The foam according to claim 16, wherein the ethylenically unsaturated monomer capable of providing a cationic charge to the polymer composition comprises a quaternized amine monomer.

21. The foam according to claim 16, wherein the ethylenically unsaturated monomer capable of providing a cationic charge to the polymer composition comprises a quaternary derivative capable of providing hydrophobicity to the polymer composition, wherein the quaternary derivative is an ethylenically unsaturated monomer that comprises a quaternary ammonium salt, and wherein the quaternary ammonium salt comprises one or more alkyl groups having two to twenty carbons.

22. The foam according to claim 16, wherein the monomer having alkoxylated functionality is selected from the group consisting of:
(a) $CH_2=C(R)COO(CH_2CHR'O)_nR''$, where R is H or $C_1$-$C_4$ alkyl; R' is H or $C_1$-$C_4$ alkyl; R'' is H or $C_1$-$C_{12}$ alkyl; and n is 1-30;
(b) $CH_2=C(R)COO(CH_2CH_2O)_n(CH_2CHR'O)_mR''$, where R is H or $C_1$-$C_4$ alkyl; R' is H or $C_1$-$C_4$ alkyl; R'' is H or $C_1$-$C_{12}$ alkyl; and n and m each is 1-15;
(c) $CH_2=C(R)COO(CH_2CHR'O)_n(CH_2CH_2O)_mR''$, where R is H or $C_1$-$C_4$ alkyl; R' is H or $C_1$-$C_4$ alkyl; R'' is H or $_1$-$C_{12}$ alkyl; and n and m each is 1-15; and
(d) mixtures of (a) and (b).

23. The foam according to claim 16, wherein the polymer composition further includes up to about 1.0 weight percent of a nonionic surfactant.

24. The foam according to claim 16, wherein the polymer composition further includes an antimicrobial agent or antistatic agent.

25. The foam according to claim 24, wherein the antimicrobial agent is a chitosan material.

26. The foam according to claim 24, wherein the antimicrobial agent is a metal biocide selected from the group consisting of silver and zinc, and salts and oxides thereof.

27. The foam according to claim 24, wherein the antistatic agent is selected from the group consisting of nitrogen compounds, esters of fatty acids, polyhydric alcohols, solutions of electrolytes in liquids with high dielectric constants, metallic salts and oxides, metals, carbon black, carbon nanotubes and semiconductors.

28. The foam according to claim 24, wherein the antimicrobial agent is undecylenic acid or alcohol or a reaction product of undecylenic acid with hydroxyl or acid containing material having ethylenic unsaturation.

29. A polymer material having antimicrobial and/or antistatic properties, said polymeric material comprising a base polymer blended with a cationically charged polymer composition consisting essentially of about 20 to about 99 weight percent of a noncationic ethylenically unsaturated monomer, about 0.5 to about 75 weight percent of an ethylenically unsaturated monomer capable of providing a cationic charge to the polymer composition, about 0.5 to about 75 weight percent of a steric stabilization monomer and 0 to 1.0 weight percent of a nonionic surfactant, wherein cationically-charged polymer composition is devoid of cationic and anionic surfactants, wherein the steric stabilization component is a polymerizable surfactant, a monomer having alkoxylated functionality, or is a protective colloid.

30. The polymeric material according to claim 29, wherein the noncationic ethylenically unsaturated monomer is selected from the group consisting of vinyl aromatic monomers; olefins; aliphatic conjugated diene monomers; non-aromatic unsaturated mono- or dicarboxylic ester monomers; monomers based on the half ester of an unsaturated dicarboxylic acid monomer; unsaturated mono- or dicarboxylic acid monomers and derivatives thereof; nitrogen-containing monomers; phosphorous-containing monomers; sulfur-containing monomers; and vinyl ester monomers.

31. The polymeric material according to claim 29, wherein the ethylenically unsaturated monomer capable of providing a cationic charge to the polymer composition comprises an amine or amide monomer.

32. The polymeric material according to claim 29, wherein the ethylenically unsaturated monomer capable of providing a cationic charge to the polymer composition comprises a quaternized amine monomer.

33. The polymeric material according to claim 29, wherein the ethylenically unsaturated monomer capable of providing a cationic charge to the polymer composition comprises a quaternary derivative capable of providing hydrophobicity to the polymer composition, wherein the quaternary derivative is an ethylenically unsaturated monomer that comprises a quaternary ammonium salt, and wherein the quaternary ammonium salt comprises one or more alkyl groups having two to twenty carbons.

34. The polymeric material according to claim 29, wherein the monomer having alkoxylated functionality is selected from the group consisting of
(a) $CH_2=C(R)COO(CH_2CHR'O)_nR''$, where R is H or $C_1$-$C_4$ alkyl; R' is H or $C_1$-$C_4$ alkyl; R'' is H or $C_1$-$C_{12}$ alkyl; and n is 1-30;
(b) $CH_2=C(R)COO(CH_2CH_2O)_n(CH_2CHR'O)_mR''$, where R is H or $C_1$-$C_4$ alkyl; R' is H or $C_1$-$C_4$ alkyl; R'' is H or $C_1$-$C_{12}$ alkyl; and n and m each is 1-15;

(c) $CH_2\!=\!C(R)COO(CH_2CHR'O)_n(CH_2CH_2O)_mR''$, where R is H or $C_1$-$C_4$ alkyl; R' is H or $C_1$-$C_4$ alkyl; R" is H or $C_1$-$C_{12}$ alkyl; and n and m each is 1-15; and (d) mixtures of (a) and (b).

35. The polymeric material according to claim 29, wherein the polymer composition further includes an antimicrobial agent or antistatic agent.

36. The polymeric material according to claim 35, wherein the antimicrobial agent is a chitosan material.

37. The polymeric material according to claim 35, wherein the antimicrobial agent is a metal biocide selected from the group consisting of silver and zinc, and salts and oxides thereof.

38. The polymeric material according to claim 35, wherein the antistatic agent is selected from the group consisting of nitrogen compounds, esters of fatty acids, polyhydric alcohols, solutions of electrolytes in liquids with high dielectric constants, metallic salts and oxides, metals, carbon black, carbon nanotubes, and semiconductors.

39. The polymeric material according to claim 35, wherein the antimicrobial agent is undecylenic acid, or alcohol or a reaction product of undecylenic acid with hydroxyl or acid containing material having ethylenic unsaturation.

40. The polymeric material according to claim 35, wherein said base polymer is selected from the group consisting of polyurethanes, phenolics, polyesters, polyolefins, polyamides, polycarbonates, polyethers, polyether-amides, polyetherimides, polyorganosilanes, polysulfones, polyisoprene, polychloroprene, acrylics, styrene-butadienes, styrene acrylonitriles, ABS, EVA, polytetrafluoroethylene, polyether-esters, and polyepoxides.

41. The polymeric material according to claim 35, wherein the polymeric material is a solid.

42. The polymeric material according to claim 35, wherein the polymeric material is a foam.

43. A shampoo, lotion, cream, body wash, or cosmetic, comprising a cationically-charged polymer composition comprising a noncationic ethylenically unsaturated monomer, an ethylenically unsaturated monomer capable of providing a cationic charge to the polymer composition and a steric stabilization component incorporated into the cationically-charged polymer composition, wherein the steric stabilization component is a polymerizable surfactant, a monomer having alkoxylated functionality, or is a protective colloid.

44. The shampoo, lotion, cream, body wash, or cosmetic of claim 43, wherein the noncationic ethylenically unsaturated monomer is selected from the group consisting of vinyl aromatic monomers; olefins; aliphatic conjugated diene monomers; non- aromatic unsaturated mono- or dicarboxylic ester monomers; monomers based on the half ester of an unsaturated dicarboxylic acid monomer; unsaturated mono- or dicarboxylic acid monomers and derivatives thereof; nitrogen-containing monomers; phosphorous-containing monomers; sulfur-containing monomers; and vinyl ester monomers.

45. The shampoo, lotion, cream, body wash, or cosmetic of claim 43, wherein the ethylenically unsaturated monomer capable of providing a cationic charge to the polymer composition comprises an amine or amide monomer.

46. The shampoo, lotion, cream, body wash, or cosmetic of claim 43, wherein the ethylenically unsaturated monomer capable of providing a cationic charge to the polymer composition comprises a quaternized amine monomer.

47. The shampoo, lotion, cream, body wash, or cosmetic of claim 43, wherein the monomer having alkoxylated functionality is selected from the group consisting of:

(a) $CH_2\!=\!C(R)COO(CH_2CHR'O)_nR''$, where R is H or $C_1$-$C_4$ alkyl; R' is H or $C_1$-$C_4$ alkyl; R" is H or $C_1$-$C_{12}$alkyl; and n is 1-30;

(b) $CH_2\!=\!C(R)COO(CH_2CH_2O)_n(CH_2CHR'O)_mR''$, where R is H or $C_1$-$C_4$ alkyl; R' is H or $C_1$-$C_4$ alkyl; R" is H or $C_1$-$C_{12}$ alkyl; and n and m each is 1 1-15;

(C) $CH_2\!=\!C(R)COO(CH_2CHR'O)_n(CH_2CH_2O)_mR''$, where R is H or $C_1$-$C_4$ alkyl; R' is H or $C_1$-$C_4$ alkyl; R" is H or $C_1$-$C_{12}$alkyl; and n and m each is 1-15; and (d) mixtures of (a) and (b).

\* \* \* \* \*